United States Patent [19]
Chilcoat

[11] Patent Number: 5,846,183
[45] Date of Patent: Dec. 8, 1998

[54] ARTICULATED ENDOSCOPE WITH SPECIFIC ADVANTAGES FOR LARYNGOSCOPY

[76] Inventor: Robert T. Chilcoat, 665 Donald Dr. North, Bridgewater, N.J. 08807

[21] Appl. No.: 888,450

[22] Filed: Jul. 7, 1997

Related U.S. Application Data

[63] Continuation of Ser. No. 473,756, Jun. 7, 1995, abandoned.

[51] Int. Cl.[6] .................................................. A61B 1/00
[52] U.S. Cl. ........................ 600/136; 600/120; 600/112
[58] Field of Search ................................. 600/120, 121, 600/123, 125, 101, 136, 133, 139, 141, 147, 146, 114; 433/29

[56] References Cited

U.S. PATENT DOCUMENTS

| | | | |
|---|---|---|---|
| 4,721,097 | 1/1988 | D'Amelio | 128/4 |
| 5,327,881 | 7/1994 | Greene | 600/120 |
| 5,347,989 | 9/1994 | Monroe et al. | 600/131 |
| 5,368,014 | 11/1994 | Anapliotis et al. | 600/112 |

*Primary Examiner*—Beverly M. Flanagan
*Attorney, Agent, or Firm*—Kenneth R. Schaefer

[57] ABSTRACT

A flexible fiber-optic endoscope having a plurality of independently removable modules wherein such modules contain components including a hollow body assembly with a steerable articulation section having a control means for remote manipulation, a tubular fiber-optic assembly incorporating an objective lens and an optic image guide and an optical eyepiece for viewing images carried by the image guide, and a disposable cover assembly for covering the steerable articulation section.

21 Claims, 9 Drawing Sheets

ARTICULATED ENDOSCOPE WITH SPECIFIC ADVANTAGES FOR LARYNGOSCOPY

This is a continuation of application Ser. No. 08/473,756, filed Jun. 7, 1995, now abandoned.

FIELD OF THE INVENTION

This invention relates to a fiber optic endoscope particularly suited for use as a laryngoscope and including a number of structural features and manufacturing advantages directed to making the apparatus specially adapted for facilitating placement of an endotracheal tube in a human patient under the severe time pressure frequently associated with such a procedure.

BACKGROUND OF THE INVENTION

Placement of an endotracheal (breathing) tube in the larynx of a patient to secure an open airway, either prior to surgery or during emergencies, is often a highly stressful, traumatic, and occasionally unsuccessful procedure. This procedure, called "intubation", while frequently routine, is associated with a number of possible complications. The tube can be placed in the esophagus in error and, if this error is not noted, patient injury or death can result. In addition, placement is usually time critical, and failure to secure the airway in time in a non-breathing patient can also result in patient injury or death.

Correct placement of an endotracheal tube requires either visualization of appropriate anatomical landmarks to insure that the tube has entered the correct passageway (trachea rather than esophagus), or use of some auxiliary device that can guarantee correct placement regardless of a particular patient's deviation from normal due to anatomical variability, disease state, or traumatic injury. For the former, a wide variety of devices, generically called "laryngoscopes" have been described and patented. (See, for example, U.S. Pat. No. 4,905,669, granted Mar. 6, 1990 to Bullard et al. and references cited therein and U.S. Pat. No. 5,279,281, granted Jan. 18, 1994 to Harvey.) These optical devices are intended to permit visualization of appropriate anatomical landmarks (usually the vocal cords) in a wide variety of normal and abnormal circumstances. The latter devices, such as intubating stylets, guides, oral airways and the like, usually exploit some feature or shape of the anatomy to insure blind placement, and will not be described further here.

The prior art of laryngoscopes can be conveniently divided into rigid laryngoscopes, which may or may not have a fiber optic imaging means, and flexible endoscopes and bronchoscopes such as is shown in the patents first mentioned above and, for example, in U.S. Pat. No. 5,183,031 granted Feb. 2, 1993 to Rossoff which can be used for laryngoscopy. Some flexible bronchoscopes intended primarily for laryngoscopy may be sold as "fiber-optic laryngoscopes". All laryngoscopes also carry a source of light to illuminate the anatomy. To further confuse the nomenclature, many modern rigid laryngoscopes use fiber-optic illumination fibers to carry the illumination light from a light source mounted in the handle to the tip. These are also frequently called "fiber-optic laryngoscopes".

The trachea in humans begins just below the base of the tongue, and, because of its location and orientation—normally at a right angle to the longitudinal axis of the mouth—direct visualization into the trachea requires that the patient's neck be extended significantly, and that his or her tongue be compressed so that a direct line of sight can be established. Rigid laryngoscopes are designed either to provide this straight line of sight, or to provide some other means of seeing "around the corner". To achieve the latter, mirrors, prisms, and fiber-optic image guides have been used. Once the vocal cords or other landmarks are visualized, the distal end of an endotracheal tube is inserted into the trachea while observing that it passes into the correct opening and not into the esophagus.

A flexible fiber-optic bronchoscope or laryngoscope is used in a very different manner. In this device, a flexible fiber-optic image guide, incorporating an objective lens on the distal end, and an eyepiece on the proximal end, is used to observe the anatomy as the scope is advanced into the patient's mouth. As the base of the tongue is reached, a short, controllable segment at the tip of the scope is deflected anteriorly by means of a remotely controlled articulating mechanism towards the trachea and is advanced. As the scope is advanced further, it is directed by manipulation and modification of the deflection of the tip to pass through the vocal cords and into the trachea. The vocal cords are again the landmark indicating correct placement, but in this case they indicate that the tip of the bronchoscope has passed into the trachea.

Once the bronchoscope is correctly placed, a hollow endotracheal breathing tube, which was threaded over the bronchoscope before the start of the procedure, is slipped down the flexible bronchoscope shaft so that it passes into the trachea over the bronchoscope. This part of the procedure is performed blindly, but since the bronchoscope is in the trachea, the endotracheal tube is guided automatically there as well.

Correct placement of the flexible fiber-optic bronchoscope into the trachea is hampered by features of its customary design. In many cases, the articulation of the tip is in a single plane (two-way articulation). It is necessary to rotate the entire bronchoscope to observe or to advance the instrument to one side or the other off the midline. Since some patients have tracheas that are deviated to the side, this off-line insertion requires additional time and skill. In addition, the customary design of the flexible fiber-optic bronchoscope includes a bulky, heavy handle that is difficult to manipulate, particularly in the stressful environment in which intubation is generally performed.

Furthermore, the conventional flexible fiber-optic bronchoscope is a relatively complex structure, and is therefore expensive and difficult to clean. This makes the apparatus less available in emergencies, since it is unusual for a treatment facility to allocate sufficient resources to purchase more than a small number of instruments, and the few that are available may not be clean from their last use. The high cost of such apparatus is furthermore due to the complexity of the articulation mechanism employed and to the costly fiber optic image bundle. Conventional articulation mechanisms use a large number of discrete "vertebrae", which may or may not be hinged together, and which are threaded over one or more pull wires. When tension in a pull wire is increased by manipulation of the remote control handle, the vertebrae are forced together on the side associated with the particular wire, causing the assembly to bend in that direction. The labor necessary to assemble these individual vertebrae is a significant contributor to the high cost of such devices.

In addition, flexible fiber-optic bronchoscopes usually incorporate one or more internal passages ("working channels"). Sputum and other patient secretions can collect in these, and they must be cleaned out after each use. The present invention provides substantial advantages in overcoming difficulties of the prior art in this regard.

Finally, a conventional flexible fiber-optic bronchoscope, because of its complex construction, requires return to a factory service center for repair. This further reduces its availability in an emergency. The present invention provides additional advantages in this regard as well.

SUMMARY OF THE INVENTION

In view of problems associated with flexible fiber-optic bronchoscopes for use in the time-critical, high pressure environment of most intubations, a primary object of the present invention is to increase the ease of use of a flexible fiber-optic device, while increasing its availability, by design and manufacturing features that significantly reduce its cost and improve ease of cleaning and repair.

The invention envisions use of a number of separate modules, with each such module containing components which themselves may be incorporated into other modules, exchanged with components of other modules or themselves comprise a distinct independent module. In accordance with a preferred embodiment of the present invention, a plurality of (e.g., four) modules assemble into the total instrument. The instrument is made up of a first module comprising a hollow, tubular carrier or shaft ("articulation module") that incorporates a control handle for the operator, a joystick control to remotely manipulate the distal tip of the carrier, a hollow flexible section that carries control wires in its wall, and an articulating section that bends in any direction in response to movements of the joystick control. A second module comprises a tubular assembly ("fiber-optic module") that fits inside the hollow tubular carrier of the articulation module, is readily removable and detachable from the articulation module and incorporates a fiber optic image guide, and an objective lens to focus an image onto the tip of the image guide. Additional optical fibers to carry illumination light to the tip, and a connector for supplying light from an external light source to the illumination carrying fibers are included either as part of the fiber optic module or, alternatively, may be separate from such fiber optic module or even included, instead, as part of the first or articulation module. The instrument further comprises a third module comprising an optical eyepiece ("eyepiece module") that mounts into the proximate end of the handle of the first or articulation module and permits the user to observe the image carried by the image guide incorporated into the fiber optic module by means of a set of lenses which may be focused by means of rotating and advancing or retracting the eyepiece module in a conventional manner. The instrument further comprises a fourth module comprising a tubular disposable cover into which the first and second modules slide, which incorporates an optical window in its distal tip, and which may optionally carry additional passages as working channels. This last module protects the first and second modules from contamination, and may be discarded after use, significantly reducing the need to clean the other modules after ordinary use.

An additional object of the invention is to provide an ergonomic design and controls that are intuitive to use, so that reduced skill is required to accomplish the intubation procedure for which the invention is primarily intended.

DETAILED DESCRIPTION OF THE PREFERRED EMBODIMENT

Figure 1:
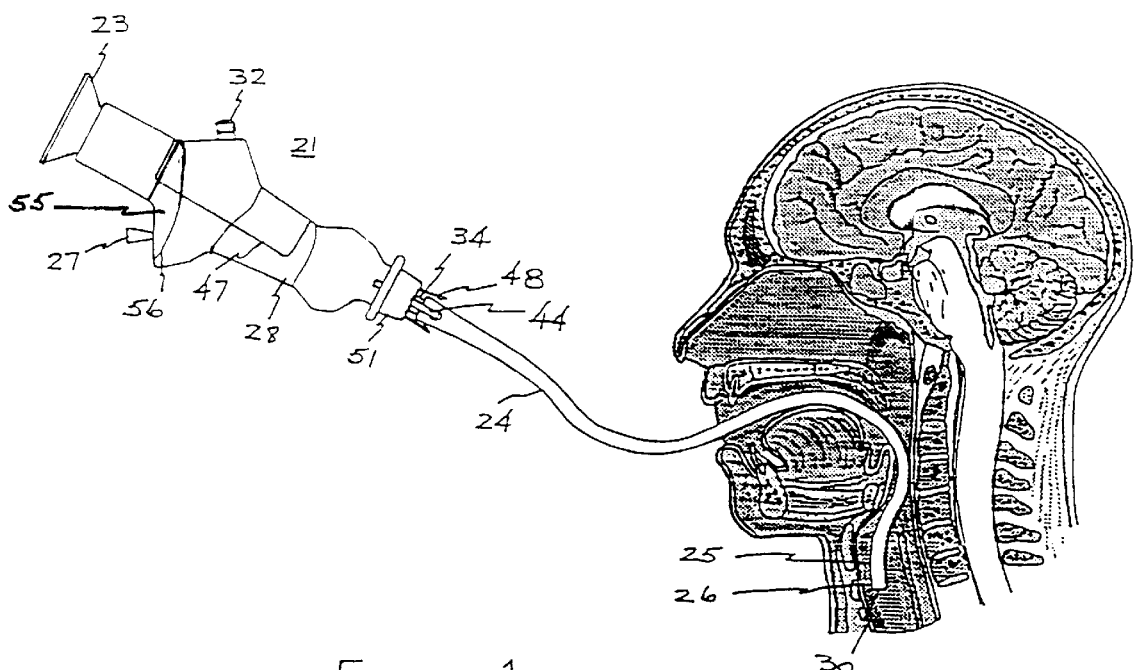
FIG. 1 is a pictorial representation of one embodiment of the invention inserted in a patient in the manner in which it would be used as an intubation apparatus.
Figure 2:
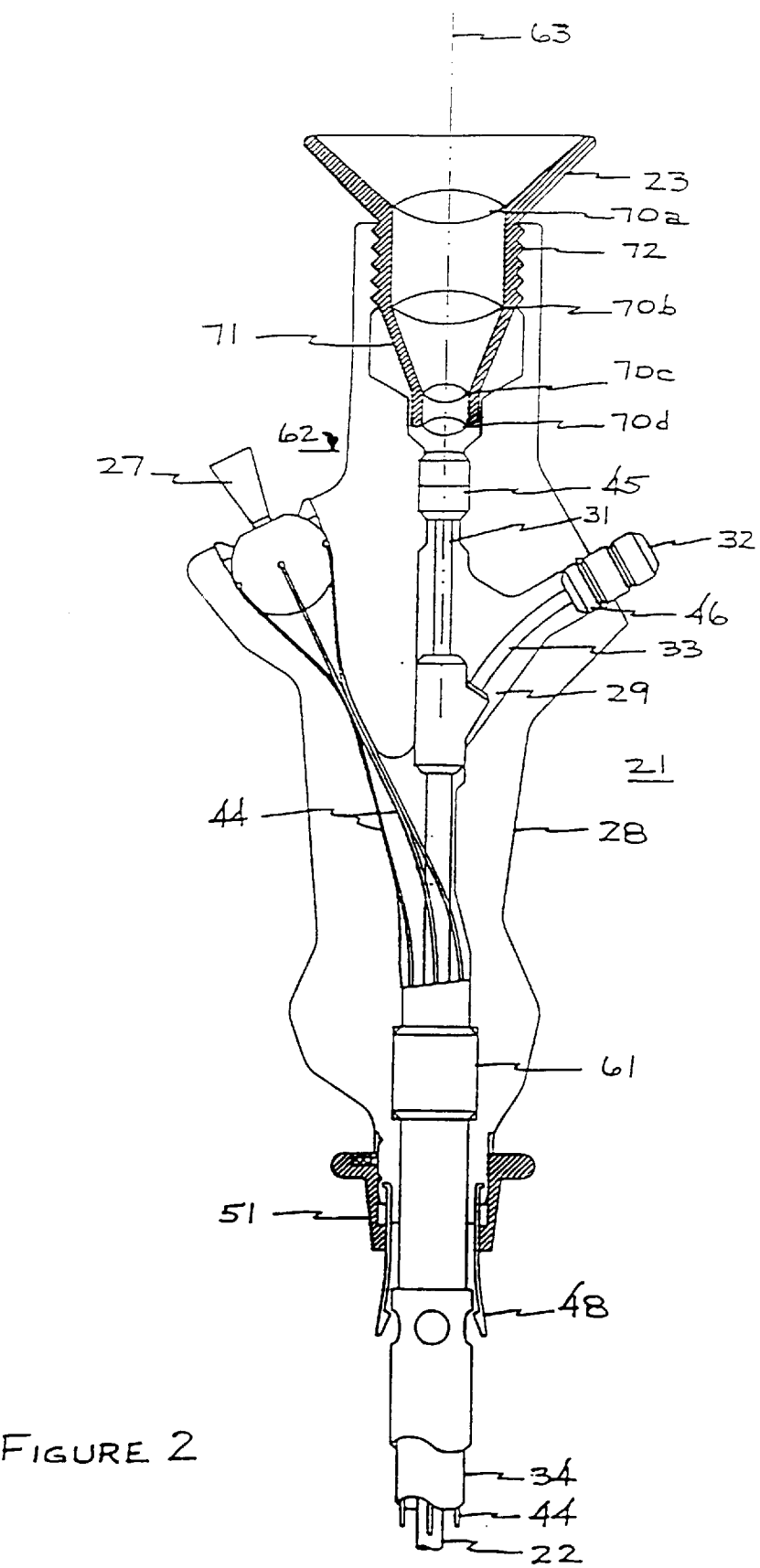
FIG. 2 is a cutaway front view of a half-section of the handle portion of the first module, illustrating the relationships with the second, third and fourth modules.

Referring to FIGS. 1 and 2, a flexible fiber-optic endoscope (bronchoscope) comprises first, second, third and fourth modules 21, 22, 23, 24. First or articulation module 21 comprises a flexible shaft 34 having a steerable section 25 near its distal end 26 that is controlled remotely by means of a joystick or similar control 27. First module 21 also includes a hollow handle portion 28 which is grasped by the user so as to permit manipulation of the overall assembly in use. As can be seen in FIG. 2, the second or fiber optic module 22 terminates inside a cavity or hollow tubular carrier 29 of handle 28 at a plane 62 along an optical axis 63 of the third or optical eyepiece module 23 so that a user can observe an image conducted from a distal tip 30 of a flexible fiber optic image guide bundle 31. Image guide 31 extends to the distal end 26 of steerable section 25 to permit viewing at the uppermost end of eyepiece module 23 of objects beyond such distal end 26. In the illustrated embodiment, fiber optic module 22 also comprises a connector 32 for attaching a light source (not shown) which may be directly attached or may be provided on an associated power supply cart, to transmit light along a set of illumination fibers 33 to the distal end 26. The optical eyepiece module 23, which is of generally conventional optical design, comprises a series of lenses shown as lenses 70a, 70b, 70c, 70d which are mounted within a combined conical—cylindrical housing 71, the housing 71 being positionable by rotation within the uppermost extremity of handle portion 28 by means of a screw thread 72. Images transmitted via the image optical guide 31 are focused by rotating (and thereby advancing or retracting) optical eyepiece module 23 with respect to handle portion 28. Optical eyepiece module 23 readily may be removed and replaced simply by screwing it all the way out of handle portion 28.

A tubular disposable cover 24, made, for example of an elastomeric polymer, that incorporates a window 35 (see FIG. 9) in its distal end comprises the fourth module of the assembly. Disposable cover 24 slips with clearance over the flexible shaft 34, protectively sealing the flexible shaft 34 and the fiber optic assembly 22 contained within shaft 34 from contamination. Cover 24 extends from the distal end 30 to the vicinity of the lower end of handle 28. When used as an intubation device, a hollow endotracheal breathing tube (not shown) is threaded over the cover 24 prior to insertion into the mouth of a patient as shown in FIG. 1.

Figure 3:
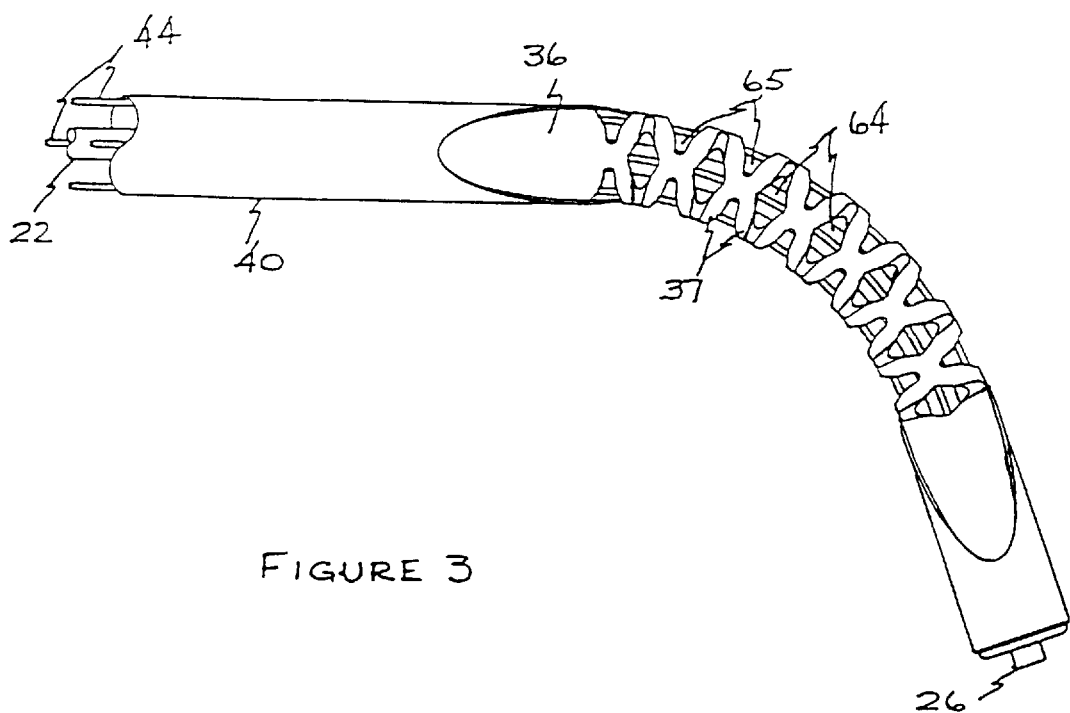
FIG. 3 is a cutaway front view of one embodiment of the articulated portion of the articulation (first) module of the assembly constructed according to the invention.
Figure 4:
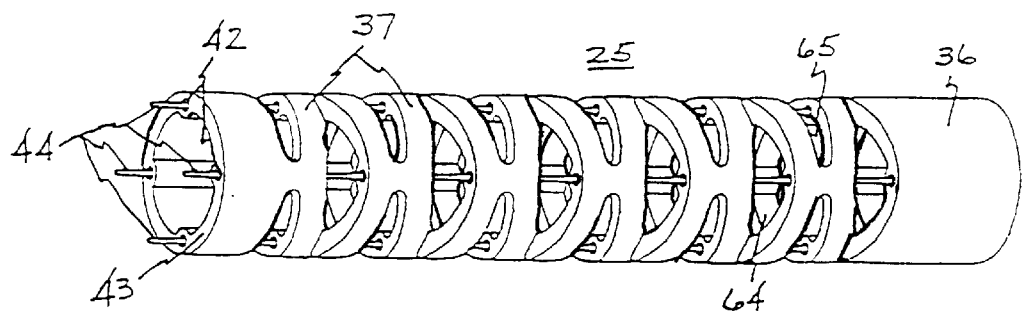
FIG. 4 is an isometric view of the articulated portion of FIG. 3, showing the relationship between the control wires and vertebrae in the articulated portion of the first module.

Referring to FIGS. 3 and 4, the steerable section 25 of the flexible shaft 34 is made controllably flexible for example, by punching out selected, generally diamond-shaped regions 64, 65 of an extruded polymer plastic sleeve 36 so as to form a series of interconnected vertebrae 37 as a single unit. These vertebrae 37 alternate in circumferential orientation along the length of sleeve 36 (i.e., are displaced 90° from each other) so that articulation in two planes (4-way articulation) may be achieved as will be described. An alternative method of forming the vertebrae 37 from a virgin extrusion is to make a series of circumferential slits in the regions where openings are desired. The polymer in the slitted region is then heated to a temperature above the glass transition temperature of the polymer and then, by stretching the sleeve longitudinally, the slits will open into the desired diamond-shaped openings. The polymer is then cooled to below the glass transition temperature to freeze the polymer in this new open configuration. As shown in FIG. 3, flexible shaft 34 also comprises a further thin tubular sleeve 40 (shown partially cut away) which covers the diamond-shaped openings 64, 65.

As shown in FIG. 4, in order to produce 4-way articulation as is desirable for this instrument, the polymer sleeve 36 forming the shaft 34 incorporates passageways 42 in its wall 43 through which control wires 44 pass. If the wires 44 are of the push-pull type, two wires, 90 degrees apart are all that is required for four way control. However, if these control wires are very thin, and with insufficient stiffness, they can only be used in tension and four are required, with one of an opposing pair relaxing as tension is applied to the opposite wire. The distal ends of wires 44 are captivated (i.e., secured with respect to the end of sleeve 36) to effect the desired movable vertebrae action when the joystick control 27 is operated.

Figure 5:
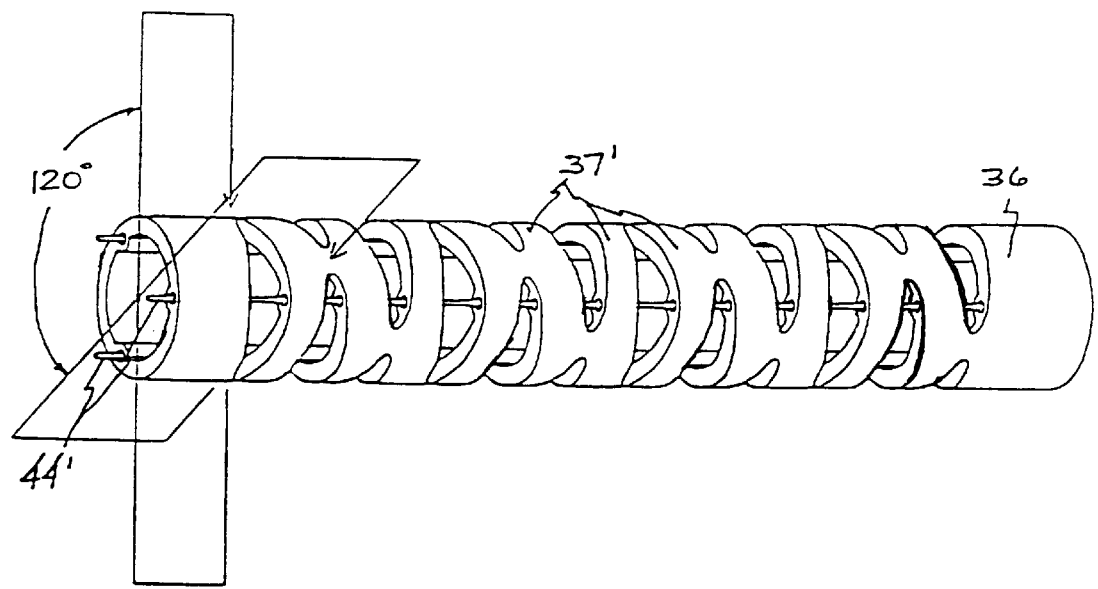
FIG. 5 is an isometric view similar to FIG. 4, showing an alternative arrangement of control wires and a different arrangement of vertebrae in the articulation mechanism.

Referring to FIG. 5, by forming vertebrae 37l in three different orientations 120 degrees apart, alternating at 0°, 120°, and 240° before repeating, it is possible to use tension-only control wires 44' but with only three wires 44' as shown in FIG. 5. It is expected that such a configuration will be advantageous from a standpoint of cost.

The plastic sleeve 36 above the portion containing vertebrae 37 is captivated within the hollow tubular carrier 29 of handle 28 by a suitable locking means such as a ferrule 61 or the like shown in FIG. 2.

Figure 6:
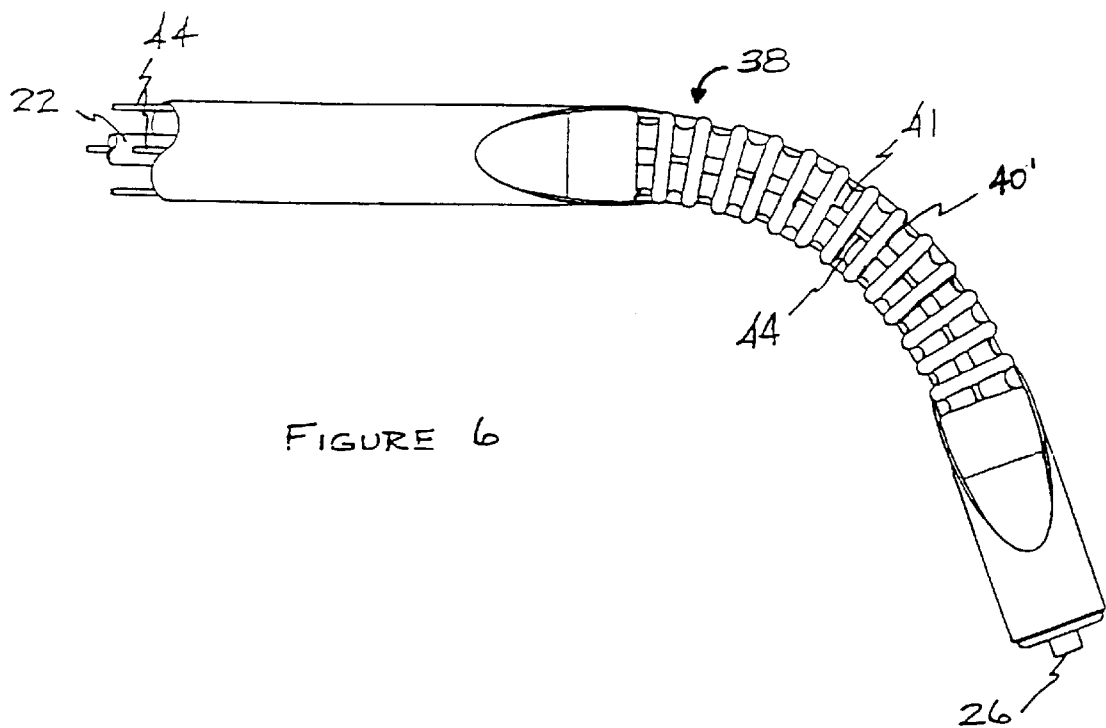
FIG. 6 is a front view of an alternative articulation mechanism including a bellows-type arrangement.

Referring to FIG. 6, as an alternative to forming vertebrae 37 from the polymer extrusion 36 itself, a bellows 38 of metallic or polymer material can be configured as the articulated section. This configuration requires that holes for control wires 40' be formed in the convolutions of the bellows 38, with spacers 41 formed between alternative sets of convolutions of bellows 38.

A bellows 38 also can be used as above with a three-wire configuration similar to FIG. 5.

Referring again to FIGS. 1 and 2, control handle 28 incorporates a joystick control 27 that applies tension to the control wires 44 when joystick 27 is moved by the user. Joystick 27 is fixedly attached to the control wires 44 and, via the handle 28 to the flexible shaft 34. The optical fiber assembly 22 slips inside the flexible shaft 34 and includes terminations 45, 46 for the image guide bundle 31 and the illumination fibers 33, respectively, contained inside the assembly. The termination 45 for the image bundle 31 is designed to be located mechanically below the eyepiece module 23 so that the optics (lenses) of eyepiece 23 focus on the end of the image bundle 31. The termination 46 for the illumination fibers 33 mounts in the handle 28 and protrudes in the form of a standard connector 32 for endoscope light sources. Access to the optical fiber assembly 22 is provided by means of a single panel (e.g., a snap-in or hinged design) area 47 which can be opened or removed by the user to permit easy replacement of either all or a portion of the assembly 22 should it become damaged or otherwise unusable. The image guide bundle 31 is generally more subject to damage and breakage than are the illumination fibers 33. It therefore may be preferable to provide easy field replacement of image guide bundle 31 separately from replacement of the overall fiber optic module 22.

Figure 7:
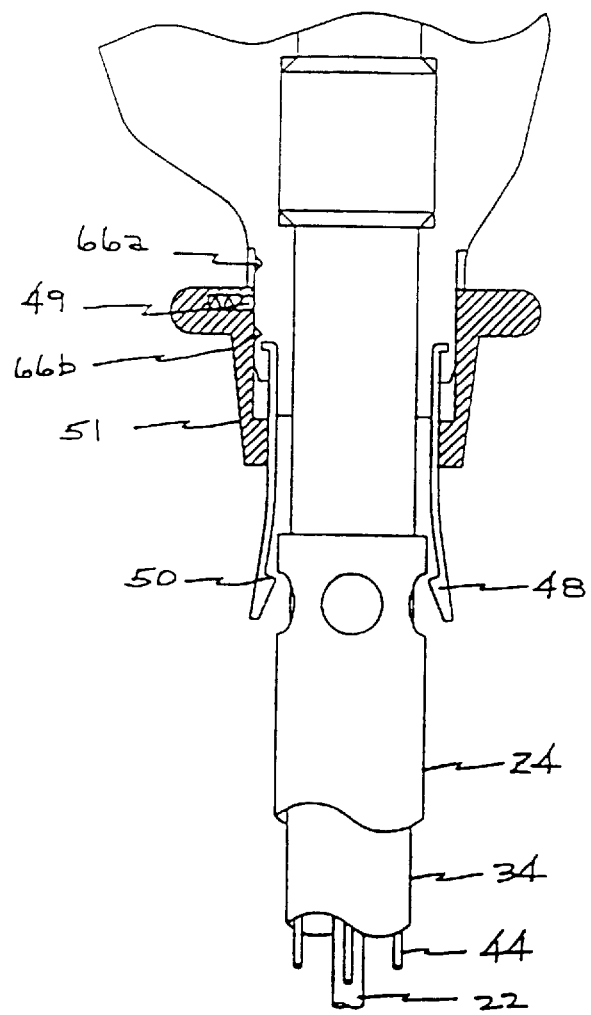
FIG. 7 is a partial detail of a portion of FIG. 2, showing one embodiment of a retention arrangement for the disposable cover.
Figure 9:
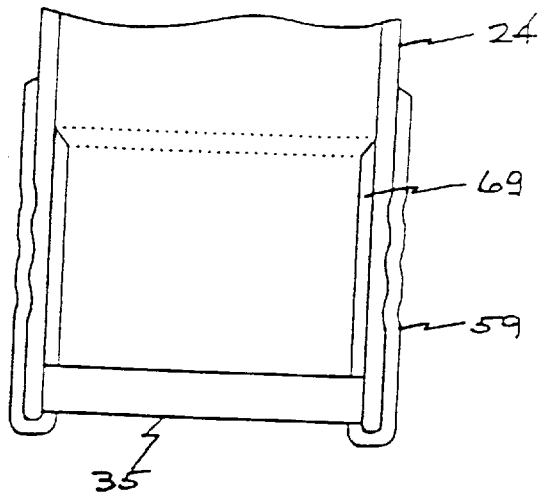
FIG. 9 is an enlarged sectional front view of one embodiment of the distal end of the disposable cover.

Referring to FIG. 9, an optical window 35 at the distal end of the disposable cover or sleeve 24 preferably is held tightly against the distal tip of the optical fiber module 22. This relationship preferably is obtained by fabricating the disposable cover 24 from an elastomeric polymer and cementing or bonding window 35 to cover 24. A metallic ferrule 59 may also be crimped onto cover 24 with an optional metallic or other backing insert 69 as shown. Furthermore, cover 24 is engaged at its upper (proximal) end by arranging a "barb" that engages the proximal end of the cover 24 as it is slightly stretched over the shaft 34 of articulation module 21. One embodiment of a suitable barb 48 is shown in FIG. 7. The disposable cover 24 may incorporate holes or lugs at its proximal end to engage teeth 50 of the barb 48. A movable sleeve 51 (or the like) is provided to cause engagement and disengagement of the teeth 50 of barb 48 when the cover 24 is to be attached or removed for disposal after use. A two detent positioning assembly comprising a spring-loaded ball 49 and upper and lower detents 66a, 66b are associated with sleeve 51 to maintain it in place in either of its positions.

Figure 8A:
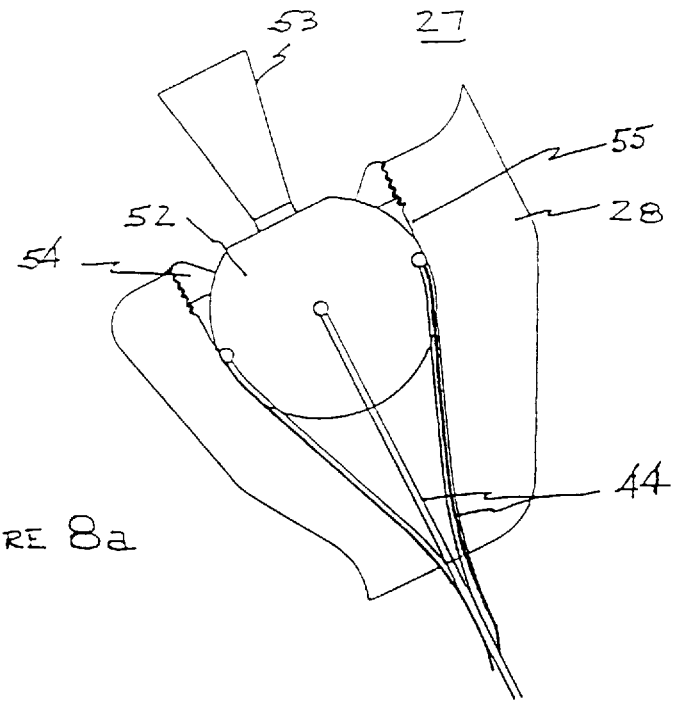
FIGS. 8a and 8b are details of alternative embodiments of the joystick articulation control of FIG. 2.

Referring to FIG. 8a, the joystick assembly 27 preferably is formed as a sphere 52 or partial sphere with a handle 53 protruding for actuation by the user's thumb or finger. The sphere 52 preferably is molded from a lubricous material such as Delrin or Teflon. Alternatively, a housing pedestal 55 that contains the sphere 52 and a retaining ring 54 can be lined with this material. The pedestal 55 that contains the joystick assembly 27 incorporates an ergonomically designed flange 56 (see FIG. 1) to guide the thumb or fingers to the joystick while providing a comfortable grip. This flange 56 is designed to be equally comfortable and to guide the thumb and fingers regardless of which hand is used to hold the instrument.

Figure 8B:
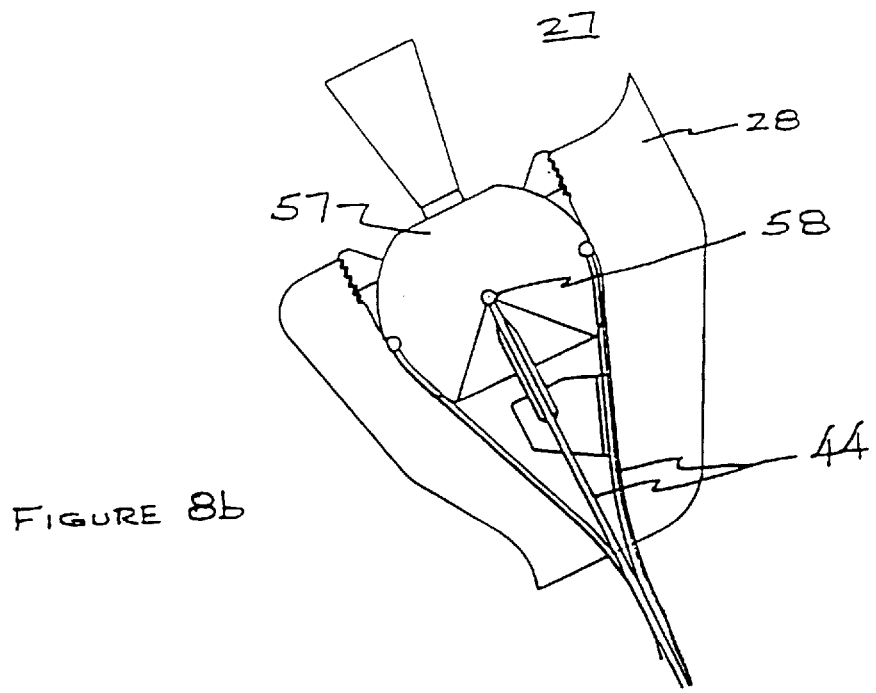

Referring to FIG. 8b, the spherical joystick assembly 27 alternatively uses a teeter-totter configuration 57 acting on a single pivot point 58.

Figure 10:
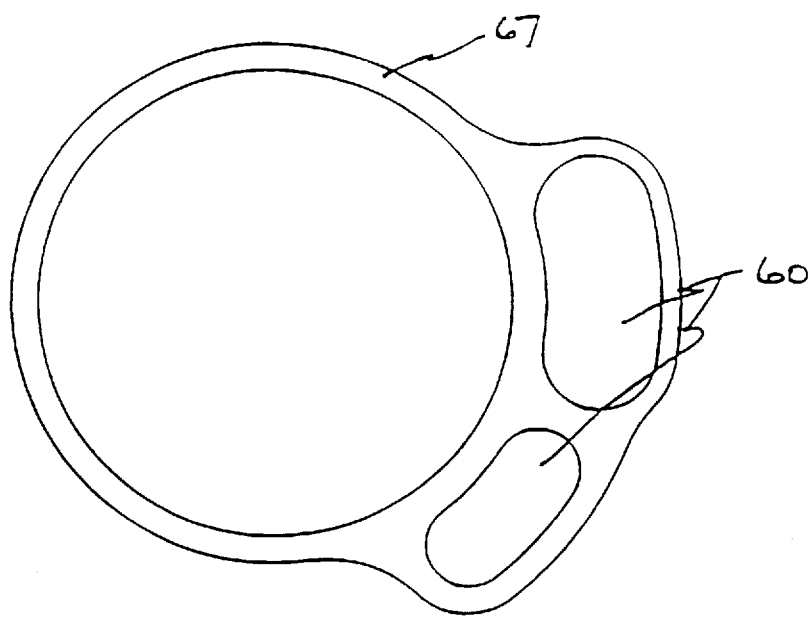
FIG. 10 is a cross section view of a disposable cover with, for example, two working channels incorporated into a side wall.

Referring to FIG. 10, an alternative disposable cover 24 is shown which incorporates one or more working channels 60 in its wall 67 or attached to its wall. These working channels 60 typically may have a round cross section, or, alternatively, may have an oval or kidney-shaped cross section as shown to reduce the overall cross section dimension of the cover 24 with channels 60. At the proximal end of the cover 24, the channel or channels 60 preferably are separated from the barb-engaging lugs (if provided) and are terminated in standard Luer or suction connectors.

Figure 11:
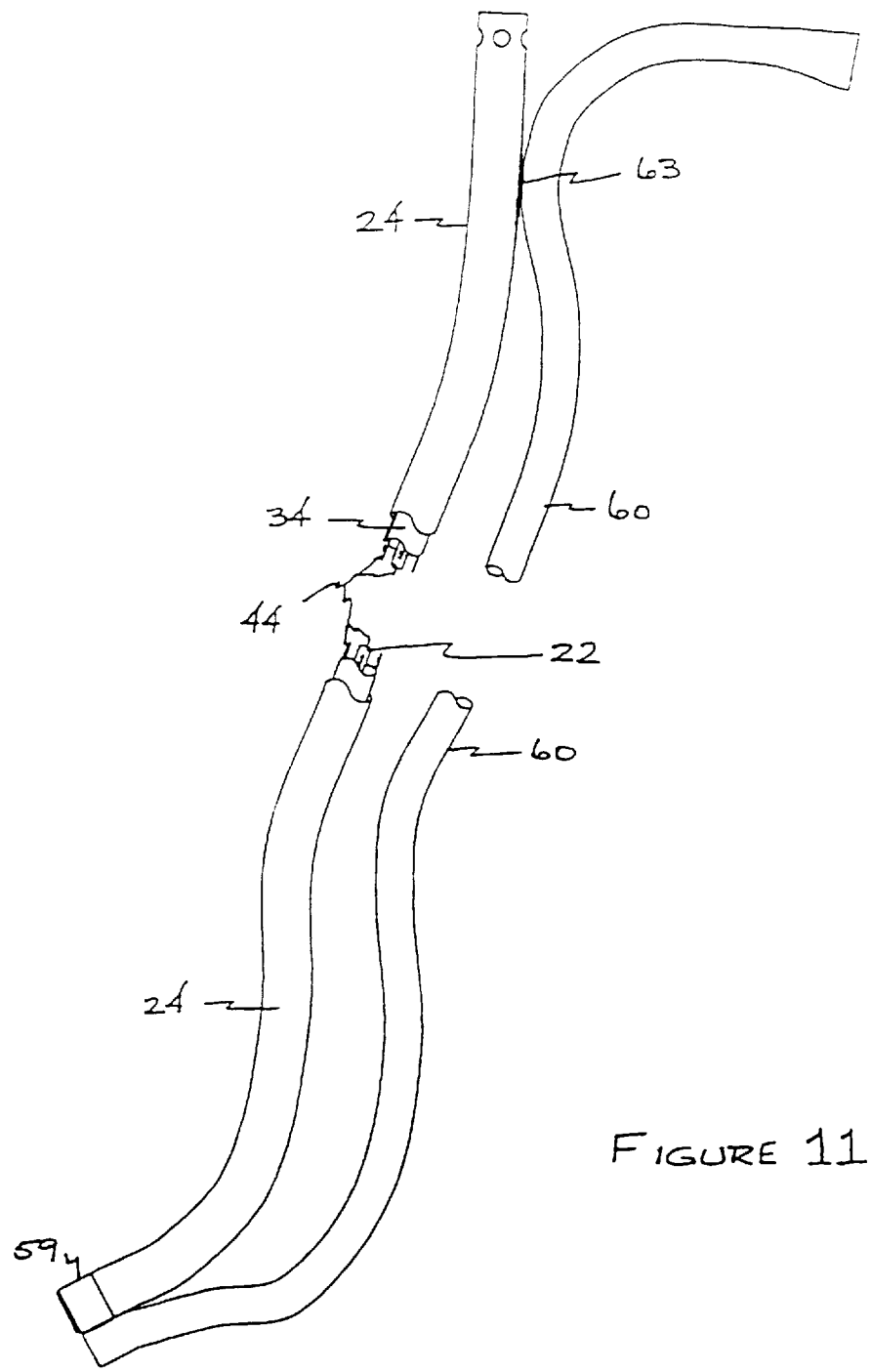
FIG. 11 is a partial isometric view of an embodiment of a disposable cover with, for example, a single working channel attached to the side wall.

Referring to FIG. 11, since the disposable cover 24 must not interfere with articulation of the assemblies contained within it, it may be necessary and desirable to separate the working channels 60 from the cover 24 along the entire length of the cover 24, attached only beyond the articulated section of shaft 34. The working channels 60 in this case may be separate extrusions, bonded to the disposable cover 24 at its tip, or to the ferrule 59, if used. The working channels 60 may also be attached to the cover 24 at a second point 63 near the proximal end of the cover 24 so that they do not tangle or get in the user's way.

Although the preferred embodiments and practical alternatives to the invention are described above by way of example, it will be understood that modifications may be made to the disclosed embodiments without departing from the scope of the invention, which is defined by the appended claims.

What is claimed:

1. A flexible fiber-optic endoscope comprising:
   a plurality of independently removable modules wherein:
      a first module comprises a hollow body assembly containing a hollow, flexible, tubular member having a steerable articulation section at a distal end thereof, said hollow body assembly including handle means for holding said endoscope during operation thereof and control means for remotely manipulating said steerable articulation section;
      a second module captivated at a proximal end within said hollow body assembly and independently removable therefrom as a module comprises a tubular fiber optic assembly incorporating an objective lens at its distal end, and an optical image guide for conducting an image formed by said objective lens to a proximal end of said fiber optic assembly; and
      a third module captivated within and independently removable from said hollow body assembly comprises an optical eyepiece assembly located at a proximal end of said hollow body assembly for viewing images carried by said image guide.

2. An endoscope according to claim 1 wherein said control means for remotely manipulating said steerable articulation section comprises a joystick.

3. An endoscope according to claim 1 wherein said steerable articulation section comprises a tubular polymer member having circumferential voids for articulation.

4. An endoscope according to claim 1 wherein said steerable articulation section comprises a bellows member for providing articulation.

5. An endoscope according to claim 1 wherein said first module comprises at least two control wires coupled to said steerable articulation section for providing four-way articulation thereof.

6. An endoscope according to claim 1 wherein said first module comprises at least three control wires coupled to said steerable articulation section for providing four-way articulation thereof.

7. An endoscope according to claim 1 and further comprising a disposable cover assembly fastened over said steerable articulation section and having an optical window at its distal tip.

8. An endoscope according to claim 7 in which said disposable cover is stretched over said flexible shaft and is held in stretched configuration by a barb assembly provided on said first module adjacent said hollow body assembly and engaging a proximal end of said cover.

9. An endoscope according to claim 8 wherein said disposable cover further comprises working channels formed in the walls thereof.

10. An endoscope according to claim 9 wherein said disposable cover further comprises working channels attached to the walls thereof.

11. An endoscope according to claim 1 wherein said first module further comprises illumination optical fibers for carrying illumination light to said distal end of said assembly and means for coupling a source of illumination light to a proximate end of said illumination optical fibers.

12. An endoscope according to claim 1 wherein said second module further comprises illumination optical fibers for carrying illumination light to said distal end of said assembly and means for coupling a source of illumination light to a proximate end of said illumination optical fibers.

13. A flexible fiber-optic endoscope comprising:
   a plurality of independently removable modules wherein:
      a first module comprises a hollow body assembly containing a hollow, flexible, tubular member having a steerable articulation section at a distal end thereof, said hollow body assembly including handle means for holding said endoscope during operation thereof and control means for remotely manipulating said steerable articulation section;
      a second module captivated at a proximal end within said hollow body assembly and independently removable therefrom as a module comprises a tubular fiber optic assembly incorporating an objective lens at its distal end, and an optical image guide for conducting an image formed by said objective lens to a proximal end of said fiber optic assembly;
      a third module captivated within and independently removable from said hollow body assembly comprises an optical eyepiece assembly located at a proximal end of said hollow body assembly for viewing images carried by said image guide; and
   wherein said steerable articulation section comprises a tubular polymer member having a pattern of circumferential slits formed therein which are thereafter caused to form vertebrae for articulation by heating and stretching said tubular member.

14. A flexible fiber-optic endoscope comprising:
   a plurality of independently removable modules wherein:
   a tubular carrier and optical eyepiece module comprises a hollow body assembly containing an optical eyepiece assembly coupled to a proximal end of said hollow body assembly, said hollow body assembly including handle means for holding said endoscope during operation thereof; and
   an articulation section and control module captivated at a proximal end within said hollow body assembly and independently removable therefrom as a module comprises a hollow, flexible, tubular member having a steerable articulation section at a distal end thereof, and control means for remotely manipulating said steerable section; and
   a fiber-optic module captivated at a proximal end within said hollow body assembly and independently removable therefrom as a module comprises a tubular fiber optic assembly incorporating an objective lens at its distal end, and-a optical image guide for conducting an image formed by said objective lens to a proximal end of said fiber optic assembly, said image being viewable through said optical eyepiece assembly.

15. An endoscope according to claim 14 wherein said steerable articulation section comprises a tubular polymer member having circumferential voids for articulation.

16. An endoscope according to claim 14 wherein said steerable articulation section comprises a bellows member for providing articulation.

17. An endoscope according to claim 14 and further comprising a disposable cover assembly module fastened over said steerable articulation section and having an optical window at its distal tip.

18. A flexible fiber-optic endoscope comprising:

a plurality of independently removable modules wherein:

a first module comprises a hollow body assembly, said hollow body assembly including handle means for holding said endoscope during operation thereof;

a tubular member module captivated at a proximal end within said hollow body assembly and independently removable therefrom as a module comprises a hollow, flexible, tubular member having a steerable articulation section at a distal end thereof, and control means for remotely manipulating said steerable articulation section;

a second module captivated at a proximal end within said hollow body assembly and independently removable therefrom as a module comprises a tubular fiber optic assembly incorporating an objective lens at its distal end, and an optical image guide for conducting an image formed by said objective lens to a proximal end of said fiber optic assembly; and a third module captivated within and independently removable from said hollow body assembly comprises an optical eyepiece assembly located at a proximal end of said hollow body assembly for viewing images carried by said image guide.

19. An endoscope according to claim 18 wherein said steerable articulation section comprises a tubular polymer member having circumferential voids for articulation.

20. An endoscope according to claim 18 wherein said steerable articulation section comprises a bellows member for providing articulation.

21. An endoscope according to claim 18 and further comprising a disposable cover assembly fastened over said steerable articulation section and having an optical window at its distal tip.

* * * * *